(12) United States Patent
Acosta

(10) Patent No.: US 8,329,620 B2
(45) Date of Patent: *Dec. 11, 2012

(54) COMPOSITIONS AND METHODS FOR INHIBITING THE AGGLOMERATION OF HYDRATES

(75) Inventor: Erick J. Acosta, Sugar Land, TX (US)

(73) Assignee: Nalco Company, Naperville, IL (US)

( * ) Notice: Subject to any disclaimer, the term of this patent is extended or adjusted under 35 U.S.C. 154(b) by 81 days.

This patent is subject to a terminal disclaimer.

(21) Appl. No.: 12/245,849

(22) Filed: Oct. 6, 2008

(65) Prior Publication Data

US 2010/0087338 A1    Apr. 8, 2010

(51) Int. Cl.
  C04B 33/04    (2006.01)
  C09K 8/68    (2006.01)
  C09K 8/524    (2006.01)
  C09K 8/60    (2006.01)
  C09K 8/54    (2006.01)
  C23F 11/14    (2006.01)
  C07D 295/00    (2006.01)
  C07C 213/00    (2006.01)

(52) U.S. Cl. .......... 507/90; 507/203; 507/239; 507/240; 507/242; 507/244; 507/263; 507/267; 507/268; 544/399; 564/281

(58) Field of Classification Search .................. 507/90, 507/203, 239, 240, 242, 244, 263, 267, 268; 544/399; 564/281
See application file for complete search history.

(56) References Cited

U.S. PATENT DOCUMENTS

| | | |
|---|---|---|
| 3,317,556 A | 5/1967 | Rose et al. |
| 3,894,962 A | 7/1975 | Allain |
| 4,652,623 A | 3/1987 | Chen et al. |
| 4,980,378 A | 12/1990 | Wong et al. |
| 6,702,946 B1 | 3/2004 | Huang et al. |
| 7,311,144 B2 | 12/2007 | Conrad |
| 7,408,004 B2 | 8/2008 | Struck et al. |
| 7,550,339 B2 | 6/2009 | Forbes |
| 2006/0094913 A1 | 5/2006 | Spratt |
| 2008/0113890 A1* | 5/2008 | Moreton et al. ............. 508/547 |
| 2010/0222239 A1 | 9/2010 | Acosta et al. |

FOREIGN PATENT DOCUMENTS

| | | |
|---|---|---|
| GB | 962242 | 7/1964 |
| WO | 0240433 | 5/2002 |
| WO | 2004032624 | 4/2004 |
| WO | 2004041884 | 5/2004 |
| WO | 2006051265 | 5/2006 |
| WO | 2008089262 | 7/2008 |

OTHER PUBLICATIONS

Synthesis, Authors: Yadav, J.S. et al. 2007, No. 22, pp. 3447-3450.*
Sharma et al., "Green and mild protocol for hetero-Michael addition of sulfur and nitrogen nucleophiles in ionic liquid", Journal of Molecular Catalysis, A: Chemical, 277, pp. 215-220, 2007.
V. Fedi et al., Insertion of an Aspartic Acid Moiety into Cyclic Pseudopeptides: Synthesis and Biological Characterization of Potent Antagonists for the Human Tachykinin NK-2 Receptor, Journal of Medicinal Chemistry, vol. 47, pp. 6935-6947, 2004.
Billmeyer, F., Textbook of Polymer Science, John Wiley & Sons, Inc., 3rd edition, p. 5, 1984.

* cited by examiner

*Primary Examiner* — John J Figueroa
*Assistant Examiner* — Atnaf Admasu
(74) *Attorney, Agent, or Firm* — Edward O. Yonter; Andrew D. Soreson

(57) ABSTRACT

One or more compositions and methods for inhibiting the formation of hydrate agglomerates in an aqueous medium that contain a specified generic formula are disclosed. The aqueous medium can be contained in an oil or gas pipeline or refinery.

27 Claims, No Drawings

COMPOSITIONS AND METHODS FOR INHIBITING THE AGGLOMERATION OF HYDRATES

FIELD OF THE INVENTION

This invention pertains to one or more compositions and methods for inhibiting the formation of hydrate agglomerates in an aqueous medium, e.g. an aqueous medium in an oil or gas pipeline or refinery.

BACKGROUND OF THE INVENTION

Since Hammerschmidt discovered in 1934 that gas hydrates would block gas pipelines, research for the prevention of hydrate formation and agglomeration has become an important matter. Gas hydrates can be easily formed during the transportation of oil and gas in pipelines when the appropriate conditions are present. Water content, low temperatures, and elevated pressure are required for the formation of gas hydrates. The formation of gas hydrates often results in lost oil production, pipeline damage, and safety hazards to field workers.

There are two approaches to prevent or slowdown the formation of gas hydrates, thermodynamic inhibitors and low dosage hydrate inhibitors (LDHIs). Thermodynamic inhibitors are substances that can reduce the temperature at which the hydrates form at a given pressure and water content. Methanol and ethylene glycol are among the most common thermodynamic inhibitors used in the oil industry. Although thermodynamic inhibitors are quite effective, they require large doses to achieve high concentration in the water phase. Thermodynamic inhibitors are regularly dosed at concentrations as high as 50% based on water content during oil and gas production. Therefore, there is a substantial cost associated with the transportation and storage of large quantities of these solvents. A more cost-effective alternative is the use of LDHIs, as they generally require less than a 2% dose based on water content to inhibit the nucleation or growth of gas hydrates. There are two general types of LDHI, kinetic hydrate inhibitors (KHIs) and anti-agglomerants (AAs/AA). KHIs work by delaying the growth of gas hydrate crystals as anti-nucleators. AAs allow the hydrates to form but they prevent them from agglomerating and subsequent accumulation into larger masses capable of causing plugs in oil and gas pipelines. An AA enables gas hydrates to form but in the shape of a fluid slurry dispersed in the liquid hydrocarbon phase. In general, the water cut should be below 50% because otherwise the slurry becomes too viscous to transport.

There is an ongoing need for new and effective methods of inhibiting the formation of hydrate agglomerates, particularly those that are capable of operating under higher water-cuts.

SUMMARY OF THE INVENTION

The invention pertains to compositions, e.g. anti-agglomerants, as well as methods for inhibiting the formation of hydrate agglomerates in an aqueous medium comprising water, gas, and optionally liquid hydrocarbon.

In one aspect, the present invention provides for a composition comprising the following formula and optionally salts thereof:

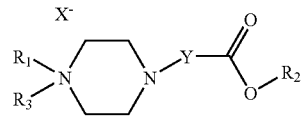

where $R_1$ is $C_nH_{2n+1}$, wherein n=0 to 12; benzyl; or H;
where $R_2$ is a $C_4$ to $C_{22}$ alkyl;
where $R_3$ is $C_nH_{2n+1}$, wherein n=0 to 12; benzyl; or H;
where $X^-$ is a halogen or a carboxylate and wherein $X^-$ is only present when both $R_1$ and $R_3$ are present;
where $Y=(CH_2)_n$, wherein n is 1 to 8; and
wherein $R_3$ and $R_1$ can not be hydrogen at the same time.

In another aspect, the present invention provides for a method of inhibiting the formation of hydrate agglomerates in an aqueous medium comprising water, gas, and optionally liquid hydrocarbon comprising adding to the aqueous medium an effective anti-agglomerant amount of a composition comprising the following formula:

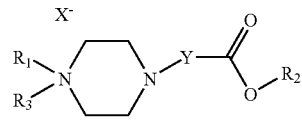

where $R_1$ is $C_nH_{2n+1}$, wherein n=0 to 12; benzyl; or H and wherein $R_1$ is linear;
where $R_2$ is a $C_4$ to $C_{12}$ alkyl;
where $R_3$ is $C_nH_{2n+1}$, wherein n=0 to 12; benzyl; or H and wherein $R_3$ is linear;
where $X^-$ is a halogen or a carboxylate and wherein $X^-$ is only present when both $R_1$ and $R_3$ are present;
where $Y=(CH_2)_n$, wherein n is 1 to 6; and
wherein $R_3$ and $R_1$ can not be hydrogen at the same time.

DETAILED DESCRIPTION OF THE INVENTION

A. Compositions

As stated above, the compositions contain a generic formula and optionally salts thereof.

In one embodiment, the alkyl groups of $R_1$ and/or $R_2$ are linear, branched, cyclic, and/or unsaturated.

In another embodiment, $R_3$ is a methyl or ethyl group. In a further embodiment, $R_3$ has a linear conformation.

In another embodiment, the halogen is chlorine, bromine, or iodine. The halogen is in ionic form when it is associated with the composition.

In another embodiment, $Y=(CH_2)_n$, wherein n is 1 to 4, optionally wherein Y is linear or branched.

In another embodiment, $R_1$ is a $C_4$-$C_6$ alkyl.
In another embodiment, $R_2$ is a $C_6$-$C_{12}$ alkyl.
In another embodiment, the composition comprises the following formula and optionally salts thereof:

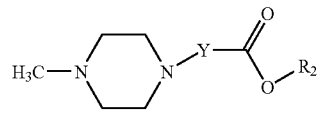

In another embodiment, the composition comprises the following formula:

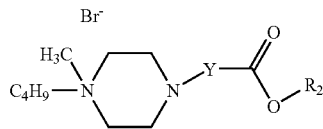

In another embodiment, the composition comprises the following formula:

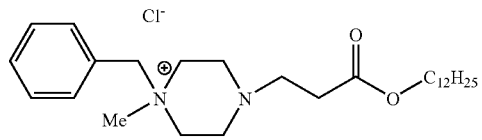

Various synthesis methodologies, which can be appreciated by one of ordinary skill in the art, can be utilized to make the claimed compositions.

In one embodiment, a composition is prepared by reacting an alkyl acrylate with 1-methylpiperazine.

In a further embodiment, the acrylate is a lauryl acrylate.

In another embodiment, the composition contains a quaternary ammonium salt prepared by reacting dodecyl 3-(4-methylpiperazin-1-yl) with an alkyl or a benzyl halide.

The compositions of this invention can contain one or more additional chemistries. Various formulations can be appreciated by one of ordinary skill in the art and can be made without undue experimentation.

In one embodiment, the composition further comprises one or more hydrate inhibitors.

In another embodiment, the composition further comprises one or more thermodynamic hydrate inhibitors, one or more kinetic hydrate inhibitors, one or more anti-agglomerants, or a combination thereof.

In another embodiment, the composition further comprises one or more asphaltene inhibitors, paraffin inhibitors, corrosion inhibitors, scale inhibitors, emulsifiers, water clarifiers, dispersants, emulsion breakers, or a combination thereof.

In another embodiment, the composition further comprises one or more polar or nonpolar solvents or a mixture thereof.

In another embodiment, the composition further comprises one or more solvents selected from isopropanol, methanol, ethanol, heavy aromatic naptha, toluene, ethylene glycol, ethylene glycol monobutyl ether (EGMBE), diethylene glycol monoethyl ether, xylene, or a combination thereof.

B. Methods

As stated above, the present invention provides for a method of inhibiting the formation of hydrate agglomerates in an aqueous medium comprising water, gas, and optionally liquid hydrocarbon comprising adding to the aqueous medium an effective anti-agglomerant amount of a composition comprising the following formula:

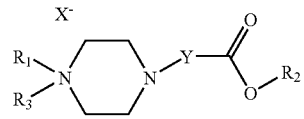

where $R_1$ is $C_nH_{2n+1}$, wherein n=0 to 12; benzyl; or H and wherein $R_1$ is linear;
where $R_2$ is a $C_4$ to $C_{12}$ alkyl;
where $R_3$ is $C_nH_{2n+1}$, wherein n=0 to 12; benzyl; or H and wherein $R_3$ is linear;
where $X^-$ is a halogen or a carboxylate and wherein $X^-$ is only present when both $R_1$ and $R_3$ are present;
where $Y=(CH_2)_n$, wherein n is 1 to 6; and
wherein $R_3$ and $R_1$ can not be hydrogen at the same time.

In another embodiment, the alkyl groups of $R_2$ are linear, branched, cyclic, and/or unsaturated.

In another embodiment, $R_3$ is a methyl or ethyl group.

In another embodiment, the halogen is chlorine, bromine, or iodine. The halogen is in ionic form when it is associated with the composition.

In another embodiment, $Y=(CH_2)_n$, wherein n is 1 to 4, optionally wherein Y is linear or branched.

In another embodiment, $R_1$ is a $C_4$-$C_6$ alkyl.
In another embodiment, $R_2$ is a $C_6$-$C_{12}$ alkyl.

In another embodiment, the composition comprises the following formula and optionally salts thereof:

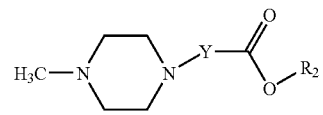

In another embodiment, the composition comprises the following formula:

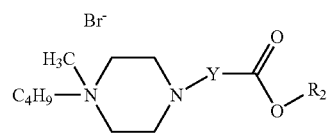

In another embodiment, the composition comprises the following formula:

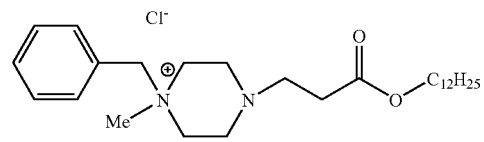

The composition is applied to an aqueous medium that contains various levels of salinity.

In one embodiment, the fluid has a salinity of 1% to 20% weight/weight (w/w) total dissolved solids (TDS).

The composition is applied to an aqueous medium that contains various levels of water cut. One of ordinary skill in the art would interpret water cut to mean the % of water in a composition containing an oil and water mixture.

In one embodiment, the water cut is from 1 to 60% w/w total dissolved solids.

Various synthesis methodologies, which can be appreciated by one of ordinary skill in the art, can be utilized to make the claimed compositions. These compositions are then utilized in methods of inhibiting the formation of hydrate agglomerates.

In one embodiment, a composition is prepared by reacting an alkyl acrylate with 1-methylpiperazine.

In a further embodiment, the acrylate is a lauryl acrylate.

In another embodiment, the composition contains a quaternary ammonium salt prepared by reacting dodecyl 3-(4-methylpiperazin-1-yl) with an alkyl or a benzyl halide.

The compositions of this invention can contain one or more additional chemistries. Various formulations can be appreciated by one of ordinary skill in the art and can be made without undue experimentation.

In one embodiment, the composition further comprises one or more hydrate inhibitors.

In another embodiment, the composition further comprises one or more thermodynamic hydrate inhibitors, one or more kinetic hydrate inhibitors, one or more anti-agglomerants, or a combination thereof.

In another embodiment, the composition further comprises one or more asphaltene inhibitors, paraffin inhibitors, corrosion inhibitors, scale inhibitors, emulsifiers, water clarifiers, dispersants, emulsion breakers, or a combination thereof.

In another embodiment, the composition further comprises one or more polar or nonpolar solvents or a mixture thereof.

In another embodiment, the composition further comprises one or more solvents selected from isopropanol, methanol, ethanol, heavy aromatic naptha, toluene, ethylene glycol, EGMBE, diethylene glycol monoethyl ether, xylene, or a combination thereof.

The aqueous medium in which the compositions and/or formulations are applied to can be contained in many different types of apparatuses, especially those that transport an aqueous medium from one point to another point, e.g. in one embodiment, the aqueous medium is contained in an oil and gas pipeline.

In another embodiment, the aqueous medium is contained in refineries, e.g. separation vessels, dehydration units, gas lines, and pipelines.

The compositions of the present disclosure and/or formulations thereof can be applied to an aqueous medium in various ways that would be appreciated by of ordinary skill in the art. One of ordinary skill in the art would appreciate these techniques and the various locations to which the compositions or chemistries can be applied.

In one embodiment, the compositions and/or formulations are pumped into the oil/gas pipeline by using an umbilical line. In a further embodiment, capillary injection systems can be utilized to deliver the surfactants, in this case anti-agglomerants. U.S. Pat. No. 7,311,144 provides a description of an apparatus and methods relating to capillary injection, which is herein incorporated by reference.

Various dosage amounts of a composition and/or formulation can be applied to the aqueous medium to inhibit the formation of hydrate agglomerates. One of ordinary skill in the art would be able to calculate the amount of anti-agglomerant for a given situation, e.g. content of aqueous medium could be a factor, without undue experimentation.

In one embodiment, the dose range for the corrosion inhibitor that is applied to an aqueous medium, e.g. aqueous medium contained in an oil/gas pipeline, is between 0.1% volume to 2% volume based on water cut.

The methodologies described in the present invention may be utilized with other compositions that are commensurate in scope with this application's disclosure. Other chemistries used for inhibiting the formation of agglomerants in fluids, which are outside the specific generic formula described above, but are commensurate in scope with the claimed compositions generic formula, may be utilized if the system conditions permit the compositions to inhibit the formation of agglomerants (hydrate agglomerates); this protocol can be achieved without undue experimentation, specifically, e.g. the rocking test described below can be utilized in determining whether a chemistry works or not.

EXAMPLES

I. Synthesis of Compositions/AA Chemicals

A. Synthesis of dodecyl 3-(4-methylpiperazin-1-yl)propanoate

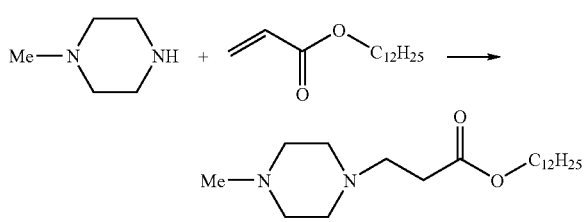

In a 40-mL scintillation vial, 12.0 g (0.05 moles) of lauryl acrylate is charged followed by the slow addition of 5.0 g (0.05 moles) of 1-methyl piperazine. The mixture is agitated using a magnetic stirrer bar and heated to 85° C. for at least 16 hours using a heating block. The final product is a light brown liquid at ambient temperature. Complete conversion is apparent from the lack of olefin protons in the $^1$H-NMR spectra. $^1$H-NMR (300 MHz, CDCl3): δ 3.83 (t, 6.6 Hz, 2H), 2.45 (t, 7.3 Hz, 2H), 2.24 (m, 10H), 2.02 (s, 3H), 1.38 (t, 6.8 Hz, 2H), 1.03 (m, 18H), 0.65 (t, 7.1 Hz, 3H). $^{13}$C-NMR (75 MHz, CDCl3): δ 171.78, 63.92, 54.64, 53.12, 52.39, 45.53, 31.93, 31.45, 29.19, 21.17, 29.12, 29.08, 28.89, 28.80, 28.20, 25.47, 22.20, 13.63.

Examples 1 to 5 are products of the reaction of commercially available alkyl acrylates with 1-methylpiperazine. The chain length of the hydrophobe portion of the surfactants ranges from butyl to behenyl ($C_{22}$). Examples 1 to 3 are soluble in methanol while examples 4 and 5 dissolve in ethylene glycol monobutyl ether (EGMBE). Examples 1 to 6 were dissolved to 20% w/w based on active ingredient for the anti-agglomeration test.

| Example | n | Solvent |
|---|---|---|
| 1 | 4 | Methanol |
| 2 | 6 | Methanol |
| 3 | 12 | Methanol |
| 4 | 18 | EGMBE |
| 5 | 18(47%), 20(10%), 22(43%) | EGMBE |

B. Synthesis of 1-butyl-4-(3-(dodecyloxy)-3-oxopropyl)-1-methylpiperazin-1-ium bromide

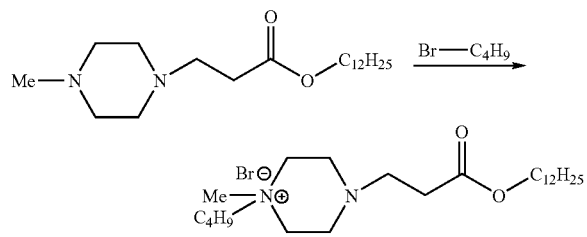

In a 100-mL round bottom flask, 5.0 g (0.015 moles) of dodecyl 3-(4-methylpiperazin-1-yl)propanoate and 7.3 g (0.044 moles) of butyl bromide are combined with 10 mL of isopropyl alcohol. This solution is heated to reflux overnight. Thin layer chromatography (TLC) was used to monitor the progress of the reaction with 1:1 methanol/toluene as a mobile phase and iodine to reveal the components on the plate. After the reaction is complete, the solvent and excess of butyl bromide are evaporated under vacuum. Finally, the resulting solid is dried under vacuum at 120° C. $^1$H-NMR (300 MHz, CDCl3): δ 3.92 (t, 5.9 Hz, 2H), 3.76 (m, 2H), 3.56 (m, 4H), 3.35 (s, 3H), 2.91 (m, 6H), 2.46 (t, 6.6 Hz, 2H), 1.67 (m, 2H), 1.47 (m, 2H), 1.12 (m, 24H), 0.74 (m, 6H). $^{13}$C-NMR (75 MHz, CDCl3): δ 170.98, 64.61, 59.14, 51.84, 45.88, 31.44, 31.28, 30.81, 29.18, 29.16, 29.13, 29.08, 28.87, 28.81, 28.11, 25.50, 25.43, 22.21, 21.96, 21.60, 13.66, 13.49.

Examples 6 to 12 are the quaternary ammonium salts of dodecyl 3-(4-methylpiperazin-1-yl)propanoate prepared from reactions with alky or benzyl halides. The chain length of the hydrophobe portion of the surfactants ranges from butyl to behenyl (e.g. mixture of $C_{18}$, $C_{20}$ and $C_{22}$). Examples 6 to 8 are soluble in methanol while examples 11 and 12 are dissolved in ethylene glycol monobutyl ether (EGMBE). Example 18 is not soluble enough to make 20% w/w (based on active ingredient) solutions in conventional organic solvents, however, other solvents may be utilized/different conditions may affect the $K_{sp}$ to allow solubility. All other examples were dissolved to 60% w/w (based on active ingredient) in their respective solvents prior to their anti-agglomeration performance evaluation. "IPA" is isopropyl alcohol.

| Example | n | $R_1$ | X" | Solvent |
|---|---|---|---|---|
| 6 | 4 | —C4H9 | Br | Methanol |
| 7 | 6 | —C4H9 | Br | Methanol |
| 8 | 12 | —C4H9 | Br | Methanol |
| 9 | 18 | —C4H9 | Br | Not soluble |
| 10 | 18(47%), 20(10%), 22(43%) | —C4H9 | Br | EGMBE |
| 11 | 12 | —C6H13 | Br | EGMBE |
| 12 | 12 | —C6H13 | Br | Methanol |
| 13 | 8 (branched, 2-ethyl hexyl) | —C4H9 | Br | IPA/MeOH |
| 14 | 4 | —C6H13 | Br | IPA/MeOH |
| 15 | 6 | —C6H13 | Br | IPA/MeOH |
| 16 | 8 (branched, 2-ethyl hexyl) | —C6H13 | Br | IPA/MeOH |
| 17 | 4 | -Benzyl | Cl | IPA/MeOH |
| 18 | 6 | -Benzyl | Cl | IPA/MeOH |

| Example | n | $R_1$ | X" | Solvent |
|---|---|---|---|---|
| 19 | 8 (branched, 2-ethyl hexyl) | -Benzyl | Cl | IPA/MeOH |
| 20 | 12 | -Benzyl |  | IPA/MeOH |

Examples 21-22 were prepared by reacting 1-ethyl piperazine with various alkyl acrylates. Specifically, Examples 21-22 are quaternary ammonium salts prepared from the reaction of the tertiary amine and 1-bromobutane in IPA at a concentration of 80% w/w solids based upon active ingredients. After the reactions are completed, as determined by TLC, the final product is diluted to 60% w/w active ingredient with methanol.

| Example | n | $R_1$ | X" | Solvent |
|---|---|---|---|---|
| 21 | 8 (branched, 2-ethyl hexyl) | —C4H9 | Br | IPA/MeOH |
| 22 | 12 | —C4H9 | Br | IPA/MeOH |

II. Anti-Agglomerate (AA) Testing

A. Rocking Cell Procedure for Anti-Agglomeration Testing on Magnolia Crude Oil A Rocking cell has two parts, a manifold and a cell body. The manifold is made up of stainless steel fittings that are welded together. It has three stems. An inlet stem is used to charge gas into the cell. An outlet stem is used to release the gas out of the cell. The third stem connects to a transducer, which measures the pressure inside of the cell. The cell body has three layers. The outer layer is a polycarbonate tube, with a thickness that is 0.7 cm. The middle layer is made of a stainless steel metal and is connected to the manifold. The inner layer contains a high-pressure sapphire tube, which has an outer diameter that is 2.8 cm, an inner diameter that is 1.85 cm, and a length that is 5 cm. This sapphire tube can handle up to 3000 psi. A stainless steel ball, which has a 1.6 cm diameter is located inside a sapphire tube to induce turbulence and mix the fluids during the rocking process.

The fluid usually contains three different components. For this Anti-Agglomerant test, 7.2 mL of warm magnolia crude oil is first injected into the cell. Next, 4.8 mL of a solution containing 7% by weight based upon actives of NaCl and deionized (DI) water was injected into the cell to make a 40% water cut mixture. AA chemicals are then put into the cell. The dosage of the AA chemical is based on the amount of aqueous phase. The initial condition for the test had a temperature of 21° C. Each cell is charged by Green Canyon gas and pressurized up to 2500 psi. The cells were rocked for at least 1.5 to 2 hours until the fluid was saturated and the pressure became stable; then the temperature was set at 4° C. The rocking sequence was the following: cells were rocked for 16 hours (simulating steady state flowing); stayed static for 6 hours; and then rocked back for 2 hours. Pressure data was recorded during this time. Observations were taken every two or three hours before the rocking was stopped and right after the start up of the rocking test.

The AAs utilized above were diluted in the appropriate solvent (See I.A. and I.B.) to a final concentration of 60% actives. The only exception is comparative example B that has a concentration of 40% actives in methanol. The solutions are then dosed to obtain a final concentration of 0.6% vol. of AA (based upon actives) in the aqueous phase. For example, a typical experiment at 40% water cut and a total volume of 12 mL will require 4.8 mL of brine, 7.2 mL of oil, and 29 μL of surfactant solution. The mixture is charged into the Rocking Cell, as described above, and a stainless steel ball is added to promote mixing during the rocking part of the experiment.

B. Anti-Agglomeration Results

The primary function of AA chemicals is to disperse hydrate particles in the oil phase while preventing them from coagulating and causing plugs. Since the hydrates are dispersed in the oil phase, as the water cut increases it becomes more difficult to achieve anti-agglomeration performance.

The AAs are diluted in the appropriate solvent (See I.A. and I.B.) to a final concentration of 60% actives. The only exception is comparative example B that has a concentration of 40% actives in methanol. The solutions are then dosed to obtain a final concentration of 0.6% vol. of AA (based upon actives) in the aqueous phase. For example, a typical experiment at 40% water cut and a total volume of 12 mL will require 4.8 mL of brine, 7.2 mL of oil, and 29 μL of surfactant (AA containing) solution. The mixture is charged into the rocking cell and a stainless steel ball is then added to promote mixing during the rocking part of the experiment. Then, the cells are placed inside a temperature-controlled tank at 21° C. and pressurized to 2500 psi with methane gas. The temperature of the rocking cell tank is gradually adjusted to 4° C. while rocking. The cells are rocked for 16 hours (simulating steady-state flowing) followed by a 6-hour shut-in, then 2 more hours of rocking.

The table below shows that the maximum water cuts that each Example or Comparative Example can handle while preventing hydrate plug formation inside the rocking cells. Comparative Example A contains no AA protection and hydrate plugs form at any water cut. Comparative Examples B and C are incumbent products used for AA applications and both of them can handle up to 40% water cut under the testing condition. Examples 1 and 2 demonstrate effectiveness similar to that of Comparative Examples B and C. It is interesting to notice that Examples 1 and 2 contain relatively short hydrophobic groups and that the hydrophilic groups are tertiary amines. Examples 3, 4, 5, and 10 failed the AA test at water cuts as low as 35%. These four Examples present long hydrophobic tails, which may cause limited solubility of the active component in the aqueous phase. Example 6 also failed at 35% water cut but the reason for the poor performance may be attributed to the combination of a short hydrophobic tail and a highly polar quaternary ammonium salt that makes the compound too soluble in the aqueous phase. Examples 7, 8, 11, and 12 demonstrated better AA performance than Comparative Examples B and C. The best overall performance is obtained with Example 8, which can handle up to 60% water cut in the rocking cells. Example 8 shows a significant improvement in water cut tolerance when compared against Comparative Examples B and C. Examples 15, 16, and 20 demonstrate good performance as anti-agglomeration LDHI (See R Rating System Table) at water cuts up to 45-50%. All other examples were tested at 40% water cut but were not able to prevent the agglomeration of gas hydrates in the rocking cells. The following table lays out when a failure/pass occurs for the experiments. Failures do not necessarily mean an absolute failure because other system conditions may result in a pass for currently failed experiments.

| LDHI Rating System | | |
|---|---|---|
| Rating | Test result | Observations |
| 1 | Fail | The rolling ball is stuck and/or the liquid level has dropped below an observable amount. |
| 2 | Fail | Large to medium agglomerants are present and/or the liquid level has dropped significantly. There is significant resistance to the rolling of the ball in the cell. |
| 3 | Marginal pass | Medium agglomerants are formed in the viewable area and/or the liquid level has dropped moderately. There is some resistance to the rolling ball in the cell. |
| 4 | Pass | Small agglomerants are formed and/or the liquid level has dropped slightly, but the solution is free flowing without hindrance. |
| 5 | Pass | Tiny and well-dispersed hydrates in the hydrocarbon phase, high liquid level, and free-flowing without hinderance. |

| Example | % Active ingredient | Dose % | Maximum Water Cut |
|---|---|---|---|
| Comparative Example A No AA | N/A | N/A | <30% |
| Comparative Example B | 60 | 1.0 | 40% |
| Comparative Example C | 40 | 1.5 | 40% |
| 1 | 60 | 1.0 | 40% |
| 2 | 60 | 1.0 | 40% |
| 3 | 60 | 1.0 | <35% |
| 4 | 60 | 1.0 | <35% |
| 5 | 60 | 1.0 | <35% |
| 6 | 60 | 1.0 | <35% |
| 7 | 60 | 1.0 | 45% |
| 8 | 60 | 1.0 | 60% |
| 10 | 60 | 1.0 | <35% |
| 11 | 60 | 1.0 | 50% |
| 12 | 60 | 1.0 | 45% |
| 13 | 60 | 1.0 | 50% |
| 14 | 60 | 1.0 | <40% |
| 15 | 60 | 1.0 | 50% |
| 16 | 60 | 1.0 | 50% |
| 17 | 60 | 1.0 | <40% |
| 18 | 60 | 1.0 | <40% |
| 19 | 60 | 1.0 | <40% |
| 20 | 60 | 1.0 | 45% |

Examples 21 and 22 demonstrated anti-agglomeration effects similar to that of Comparative Examples B and C.

| Example | % Active ingredient | Dose % | Maximum Water Cut |
|---|---|---|---|
| 21 | 60 | 1.0 | 40% |
| 22 | 60 | 1.0 | 40% |

I claim:
1. A composition comprising the following formula and optionally salts thereof:

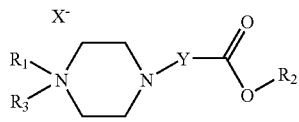

wherein $R_1$ is $C_nH_{2n+1}$, wherein n=0 to 12; benzyl; or H;
wherein $R_2$ is a $C_4$ to $C_{22}$ alkyl;
wherein $R_3$ is $C_nH_{2n+1}$, wherein n=0 to 12; benzyl; or H;
wherein $X^-$ is optional and is a halogen or a carboxylate and wherein $X^-$ is only present when both $R_1$ and $R_3$ are present;
wherein $Y=(CH_2)_n$, wherein n is 1 to 8; and
wherein $R_3$ and $R_1$ cannot be hydrogen at the same time.

2. The composition of claim 1, wherein the alkyl group of $R_1$ is linear and/or branched.

3. The composition of claim 1, wherein $R_3$ is a methyl or an ethyl group.

4. The composition claim 1, wherein the halogen is chlorine, bromine, or iodine.

5. The method of claim 1, wherein $Y=(CH_2)_n$, wherein n is 1 to 4, optionally wherein Y is linear or branched.

6. The composition of claim 1, wherein $R_1$ is a $C_4$-$C_6$ alkyl.

7. The composition of claim 1, wherein $R_2$ is a $C_6$-$C_{12}$ alkyl.

8. The composition of claim 1 comprising the following formula and optionally salts thereof:

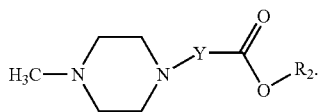

9. The composition of claim 1 comprising the following formula:

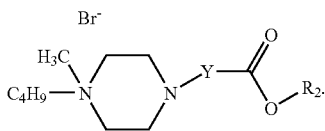

10. The composition of claim 1, wherein the composition further comprises one or more hydrate inhibitors.

11. The composition of claim 1, wherein the composition further comprises one or more thermodynamic hydrate inhibitors, one or more kinetic hydrate inhibitors, one or more anti-agglomerants, or a combination thereof.

12. The composition of claim 1, wherein the composition further comprises one or more asphaltene inhibitors, paraffin inhibitors, corrosion inhibitors, scale inhibitors, emulsifiers, water clarifiers, dispersants, emulsion breakers, or a combination thereof.

13. The composition of claim 1, wherein the composition further comprises one or more polar or nonpolar solvents or a mixture thereof.

14. The composition of claim 1, wherein the composition further comprises one or more solvents selected from isopropanol, methanol, ethanol, heavy aromatic naptha, toluene, ethylene glycol, ethylene glycol monobutyl ether (EGMBE), diethylene glycol monoethyl ether, xylene, or a combination thereof.

15. The composition of claim 1, wherein the alkyl group of $R_2$ is linear, branched, cyclic, and/or unsaturated.

16. A hydrate inhibitor comprising a quaternary ammonium salt prepared by reacting dodecyl 3-(4-methylpiperazin-1-yl) with an alkyl or a benzyl halide.

17. A method of inhibiting the formation of hydrate agglomerates in an aqueous medium comprising water, gas, and optionally liquid hydrocarbon comprising adding to the fluid an effective anti-agglomerant amount of a composition comprising the following formula:

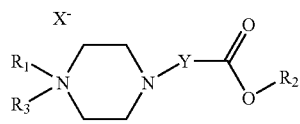

wherein $R_1$ is $C_nH_{2n+1}$, wherein n=0 to 12; benzyl; or H and wherein $R_1$ is linear;
wherein $R_2$ is a $C_4$ to $C_{12}$ alkyl;
wherein $R_3$ is $C_nH_{2n+1}$, wherein n=0 to 12; benzyl; or H and wherein $R_3$ is linear;
wherein $X^-$ is a halogen or a carboxylate and wherein $X^-$ is only present when both $R_1$ and $R_3$ are present;
wherein $Y=(CH_2)_n$, wherein n is 1 to 6; and
wherein $R_3$ and $R_1$ cannot be hydrogen at the same time.

18. The method of claim 17, wherein the alkyl groups of $R_2$ are linear, branched, cyclic, and/or unsaturated.

19. The method of claim 17, wherein $R_3$ is a methyl or ethyl group.

20. The method of claim 17, wherein the halogen is chlorine, bromine, or iodine.

21. The method of claim 17, wherein $Y=(CH_2)_n$, wherein n is 1 to 4, optionally wherein Y is linear or branched.

22. The method of claim 17, wherein $R_1$ is a $C_4$-$C_6$ alkyl.

23. The method of claim 17, wherein $R_2$ is a $C_6$-$C_{12}$ alkyl.

24. The method of claim 17, wherein said fluid has a salinity of 1% to 20% w/w percent TDS.

25. The method of claim 17, wherein said aqueous medium has a water cut from 1 to 60% w/w or v/v total dissolved solids.

26. The method of claim 17, wherein the aqueous medium is contained in an oil or gas pipeline or refinery.

27. The method of claim 17, wherein the composition comprises the following formula:

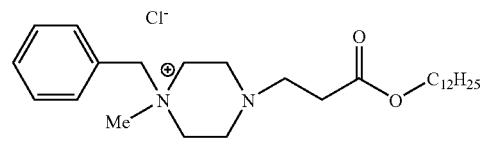

* * * * *